(12) United States Patent
King, III et al.

(10) Patent No.: US 8,109,953 B1
(45) Date of Patent: Feb. 7, 2012

(54) CATHETER DEVICE, HUB ASSEMBLY AND METHOD FOR TRAVERSING TOTAL OCCLUSIONS

(75) Inventors: Spencer B. King, III, Atlanta, GA (US); Matt D. Pursley, Alpharetta, GA (US)

(73) Assignee: Volcano Corporation, Rancho Cordova, CA (US)

( * ) Notice: Subject to any disclaimer, the term of this patent is extended or adjusted under 35 U.S.C. 154(b) by 462 days.

(21) Appl. No.: 11/838,313

(22) Filed: Aug. 14, 2007

Related U.S. Application Data

(60) Provisional application No. 60/837,899, filed on Aug. 14, 2006.

(51) Int. Cl.
*A61B 17/22* (2006.01)
*A61D 1/02* (2006.01)

(52) U.S. Cl. .................................. 606/159; 606/191

(58) Field of Classification Search .................. 606/159, 606/192, 194, 157, 108, 191–190, 275, 301; 604/96.01, 271, 104, 523, 194, 528, 533, 604/164, 264; 600/585, 29
See application file for complete search history.

(56) References Cited

U.S. PATENT DOCUMENTS

| 5,195,985 | A  | * | 3/1993  | Hall .............................. 604/195 |
| 5,527,298 | A  | * | 6/1996  | Vance et al. ................... 604/528 |
| 2003/0216771 | A1 | * | 11/2003 | Osypka et al. ................. 606/191 |
| 2004/0039371 | A1 | * | 2/2004  | Tockman et al. .............. 604/528 |
| 2005/0027236 | A1 | * | 2/2005  | Douk .............................. 604/40 |
| 2007/0021648 | A1 | * | 1/2007  | Lenker et al. ................... 600/29 |
| 2007/0149898 | A1 | * | 6/2007  | Inderbitzen et al. .......... 600/585 |

* cited by examiner

*Primary Examiner* — Ryan Severson
*Assistant Examiner* — Tin Nguyen
(74) *Attorney, Agent, or Firm* — Jeffrey L. Thompson; Thompson & Thompson, P.A.

(57) ABSTRACT

A medical device for traversing an occlusion in a vessel includes a straightening sleeve positioned at a distal aspect of a catheter, a steering sleeve having an arcuate distal end, and a guidewire disposed through the steering sleeve. The steering sleeve has a first position in which the arcuate distal end is straightened within the straightening sleeve, and a second position in which the steering sleeve extends distally past the straightening sleeve to expose the arcuate distal end. The tip of the arcuate distal end of the steering sleeve or the guidewire can be used to pierce the occlusion. An arrangement of hub assemblies with locking mechanisms and motion limiting structures facilitates adjusting and locking the relative positions of the straightening sleeve, the steering sleeve, and the guidewire. Detent mechanisms are associated with the motion limiting structures for providing controlled incremental movement of the sleeves and the guidewire.

23 Claims, 6 Drawing Sheets

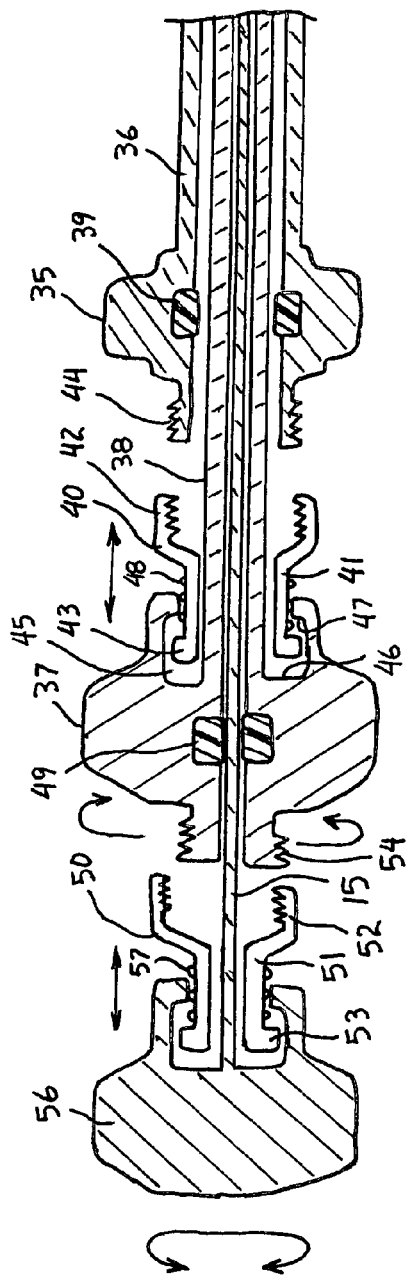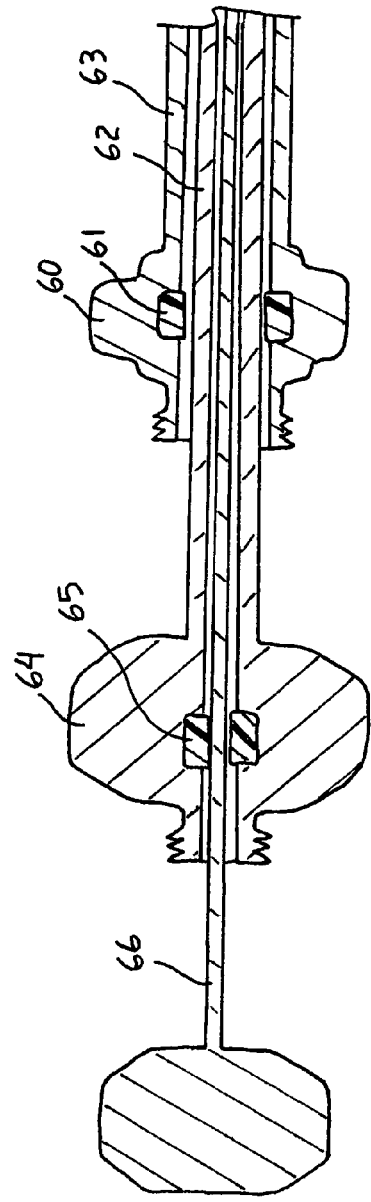

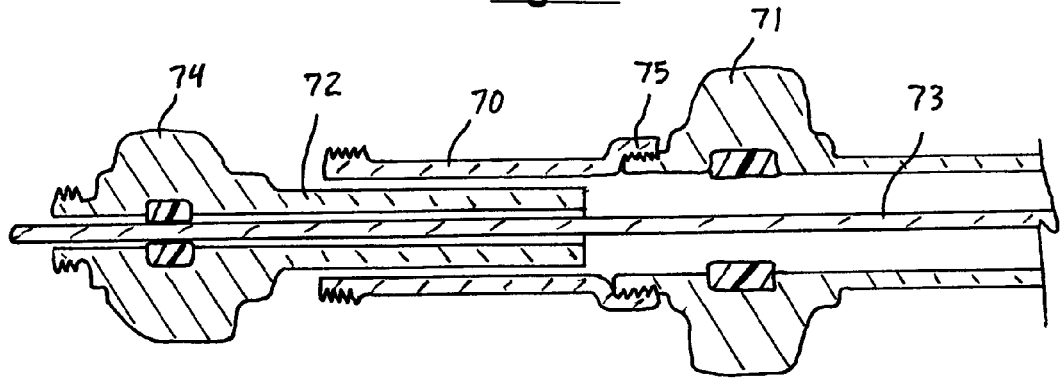
*Fig. 12*
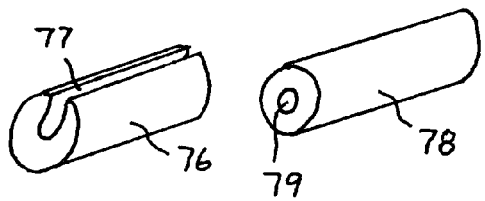
*Fig. 13*  *Fig. 14*
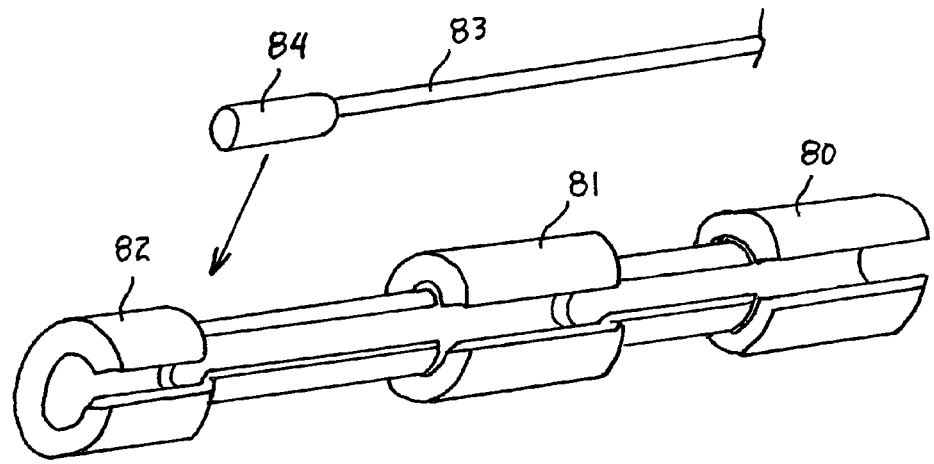
*Fig. 15*

CATHETER DEVICE, HUB ASSEMBLY AND METHOD FOR TRAVERSING TOTAL OCCLUSIONS

RELATED APPLICATIONS

This application claims priority of U.S. Provisional Application No. 60/837,899 filed on Aug. 14, 2006. The content of this prior application is incorporated herein by reference.

BACKGROUND OF THE INVENTION

1. Field of the Invention

The present invention relates generally to catheters and methods of treating the stenosis of an artery. In particular, the present invention relates to catheters and methods for puncturing, crossing and debulking chronic total occlusions (CTOs) in arteries caused by the buildup of arterial plaque tissue, and to hub assemblies used with such catheters.

2. Description of the Related Art

Chronic total occlusion (CTO) is a condition where arterial plaque tissue grows to complete stenosis of an artery and prohibits blood flow. A CTO is formed by the agglomeration of three separate physiological materials: (i) cholesterol or fat, (ii) collagen or fibrous matter, and (iii) calcium-based deposits. A CTO is also often referred to as a functional occlusion.

There are two causal pathogenic phenomena often associated with the formation of a CTO. The first is the late development of an acute occlusion. The second is the progressive occlusion of a long-term high degree stenosis. Both involve a pre-existing plaque or thrombus to which the fat and fibrous material adhere, building up until a blockage of the blood vessel occurs.

The CTO mass or CTO body, consisting of fat, fibrous matter, and calcium deposits, begins to form with fat and fibrous material attaching first. Over time the fat or cholesterol is replaced with dense collagen and calcium deposits which represents the hardened CTO body typical of this condition. The inner portion of a CTO body is softer than the distal and proximal ends which are the hardest part of a CTO body. A reduction in vessel diameter is referred to as shrinkage or negative remolding. The distal and proximal ends of a CTO are often referred to as the fibrous caps and are considered the hardest and most dense portions of a CTO.

In attempting to repair CTOs, the ability to complete a successful recanalization of a total occlusion is limited as surgeons have had difficulty crossing the CTO with a guidewire. The inability to cross a CTO with a guidewire is the principal cause of failure of the procedure to remove such blockage, as more than 50% fail for this reason. Traditional repair of a CTO proceeds through four distinct steps. First, the CTO is perforated. It is preferred that both the proximal and distal fibrous caps are perforated. Second, the lesion which gave rise to the plaque formation and ultimate CTO is debulked. Third, the blood vessel is dilated. And finally, given the high rate of reocclusion, the repaired or recanalized vessel is assisted in remaining a passable vessel by a supporting device, such as a stent.

There is a need in the industry for improved devices and methods to assist surgeons in crossing CTOs.

SUMMARY OF THE INVENTION

The present invention provides an improved medical catheter device and method for traversing an occlusion in a vessel. The device includes a straightening sleeve positioned at a distal aspect of a catheter, a steering sleeve having an arcuate distal end, and a guidewire slidable through the lumen of the steering sleeve. The steering sleeve has a first position in which the arcuate distal end is straightened within the straightening sleeve, and a second position in which the steering sleeve extends distally past the straightening sleeve to expose the arcuate distal end. The steering sleeve and straightening sleeve are sufficiently flexible without the guidewire positioned in the steering sleeve that they can pass through tortuous anatomy during a surgical procedure. The guidewire can then be inserted in the steering sleeve after the steering sleeve and straightening sleeve reach their desired position near the occlusion. The tip of the arcuate distal end of the steering sleeve or the tip of the guidewire can be used to pierce the occlusion.

The present invention also provides an arrangement of hub assemblies with locking mechanisms and motion limiting structures to facilitate adjusting and locking the relative positions of the straightening sleeve, the steering sleeve, and the guidewire. Detent mechanisms are associated with the motion limiting structures for providing controlled incremental movement of the sleeves and the guidewire.

According to a broad aspect of the present invention, a medical device is provided for traversing an occlusion in a vessel, comprising: a straightening sleeve positioned at a distal aspect of a catheter; a steering sleeve having an arcuate distal end, the steering sleeve and the straightening sleeve being slidably moveable relative to each other such that in a first position the arcuate distal end of the steering sleeve is straightened within the straightening sleeve and in a second position the steering sleeve extends distally past the straightening sleeve to expose the arcuate distal end; and a guidewire disposed through the steering sleeve within the straightening sleeve.

According to another broad aspect of the present invention, an improved arrangement of hub assemblies for a medical device is provided, comprising: a first hub assembly attached to an outer sleeve of a catheter; a second hub assembly attached to an inner sleeve of the catheter; a first locking mechanism associated with the first hub assembly, the first locking mechanism being movable between a locked condition in which the outer and inner sleeves are locked together, and an unlocked condition in which the outer and inner sleeves are moveable relative to each other; and a second locking mechanism associated with the second hub assembly, the second locking mechanism being movable between a locked condition in which the inner sleeve is locked together with a guidewire, and an unlocked condition in which the inner sleeve and the guidewire are moveable relative to each other.

According to yet another broad aspect of the present invention, a method of traversing an occlusion in a vessel is provided, comprising the steps of: providing a catheter having a straightening sleeve and a steering sleeve which are slidably moveable relative to each other such that in a first position a distal end of the steering sleeve with a preset curvature at its distal end is straightened within the straightening sleeve and in a second position the steering sleeve extends distally past the straightening sleeve to expose at least a portion of the curved distal end; inserting the catheter into a patient's body to a deployment position while maintaining the distal end of the steering sleeve straightened within the straightening sleeve; inserting a guidewire having a normally straight configuration through a lumen of the steering sleeve after the catheter has been inserted to its deployment position; sliding the steering sleeve from its first position to its second position at the deployment position; and using the steering sleeve and the guidewire positioned within the curved distal end of the steering sleeve to traverse the occlusion.

Numerous other objects and features of the present invention will be apparent to those skilled in this art from the following description wherein there is shown and described exemplary embodiments of the present invention, simply by way of illustration of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings:

FIG. 10 is a cross section view of a first hub configuration used to facilitate the relative positioning and locking of the proximal ends of the guidewire, steering sleeve and straightening sleeve of the present invention.

FIG. 11 is a cross section view of a second hub configuration used to facilitate the relative positioning and locking of the proximal ends of the guidewire, steering sleeve and straightening sleeve of the present invention.

FIG. 12 is a cross section view of a hub configuration with a guide tube according to the present invention.

FIG. 13 is a perspective view of a guide tube having a split construction for use with the hub configuration shown in FIG. 12.

FIG. 14 is a perspective view of a guide tube having a molded construction for use with the hub configuration shown in FIG. 12.

FIG. 15 is a perspective view of an assembly of guide tubes that can be snapped over the sleeves and used with the hub configuration of the present invention.

DETAILED DESCRIPTION OF THE INVENTION

A medical catheter device, hub assemblies and method according to embodiments of the present invention will now be described in detail with reference to FIGS. 1 to 17 of the accompanying drawings.

Figure 1:
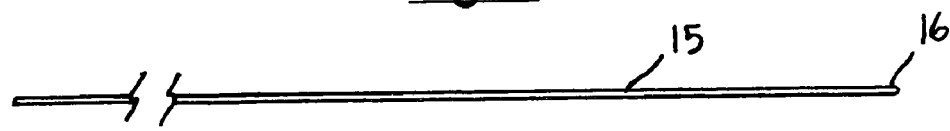
FIG. 1 is a side view of a guidewire having a normally straight configuration for use with the present invention.

A medical catheter device 10 for traversing a CTO 11 in a vessel 12 according to the present invention includes a straightening sleeve 13, a steering sleeve 14, and a guidewire 15. As shown in FIG. 1, the guidewire 15 has a normally straight configuration. The guidewire 15 may be any guidewire 15 used in catheter-based procedures and may have a blunt or sharpened shape at its distal tip 16. The shape of the distal tip 16 will depend on the particular application and the preference of the treating physician. The guidewire 15 can be made of surgical steel or any other suitable material known to one of skill in the art. The guidewire 15 can be sized in the range of 5 to 20 mils (0.005" to 0.020"), and preferably in the range of about 10 to 16 mils (0.010" to 0.016").

Figure 2:
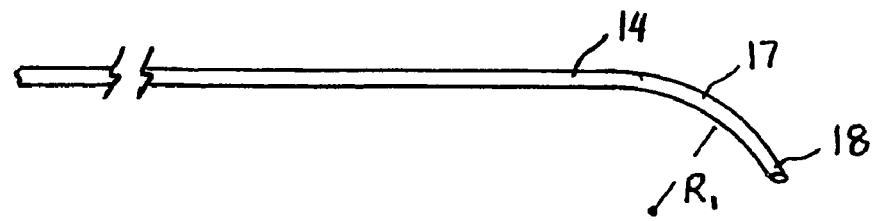
FIG. 2 is a side view of a precurved steering sleeve having a preset curve for use with the present invention.

As shown in FIG. 2, the steering sleeve 14 has a preset curvature at its distal end 17 giving it an arcuate shape with a radius of curvature R1. The steering sleeve 14 is also sometimes referred to as a J-tipped needle, J-needle, or needle sheath, and can be comprised of stainless steel, nitinol, superelastic alloys, plastic, polymer, or any other material known to one of skill in the art to be rendered flexible. The steering sleeve 14 has a shape that is arcuate at its distal end 17 yet is elastic enough and has high enough curve retention properties to be straightened without permanent deformation. The steering sleeve 14 can be covered with a protective coating, such as PTFE or other fluorinated material.

The steering sleeve 14 can be made, for example, using the non-extrusion method for catheter manufacture described in U.S. Pat. No. 6,030,371. A hard plastic, such as a high temperature thermoplastic called PEEK (poly-ether-ether-keytone), can be used as a liner for the steering sleeve 14. A wire reinforcement and powder overcoat for the steering sleeve 14 can be terminated a distance (e.g., one inch) from the distal tip 18 of the steering sleeve 14. This results in a steering sleeve 14 that looks like a normal micro catheter, but has a smaller diameter, relatively strong extension at its distal end 17. This extension can then be tipped by curving and/or machining. The distal tip 18 of the steering sleeve 14 can be machined into a blunt tip, needle tip, pointed tip or crown cur. The hard plastic of the liner used to form the distal end 17 will allow the tip shape or cut to be maintained during the surgical procedure. The distal end 17 can be curved to form the preset curvature of the steering sleeve 14 without the influence of the overcoat of powder and reinforcements.

The preset curve in the distal end 17 of the steering sleeve 14 can be set so that it is in the proper shape/orientation as it exits the straightening sleeve 13, or it can be over curved (i.e., preset with a curvature greater than what will be used during the surgical procedure). The over curvature can then be altered using the guidewire 15 during the surgical procedure, as explained below.

Figure 3:
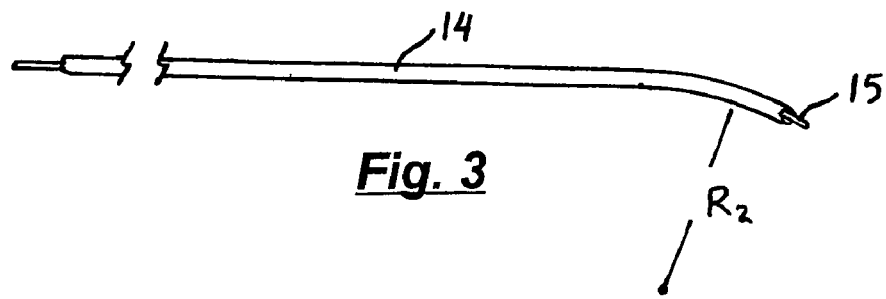
FIG. 3 is a side view of the precurved steering sleeve of FIG. 2 with the guidewire of FIG. 1 positioned in the lumen thereof, showing how the normally straight guidewire can be used to change the curvature of the steering sleeve.

As shown in FIG. 3, the guidewire 15 is slidably disposed in the lumen of the steering sleeve 14 and is moveable along the long axis of the steering sleeve 14. In this condition, the normally straight configuration of the guidewire 15 imparts a mild straightening force to the arcuate distal end 17 of the steering sleeve 14 giving it a new radius of curvature R2 and reducing the amount of its deflection off the long axis of the device 10. To compensate for this straightening force, the steering sleeve 14 can be manufactured with an over curve so that when the guidewire 15 is passed through the steering sleeve 14, the combination of over curve and the straight guidewire 15 results in the proper curve/orientation when the steering sleeve 14 exits the straightening sleeve 13. This allows the use of a much stiffer guidewire 15, which can improve the performance of the device 10 during the surgical procedure.

Figure 4:
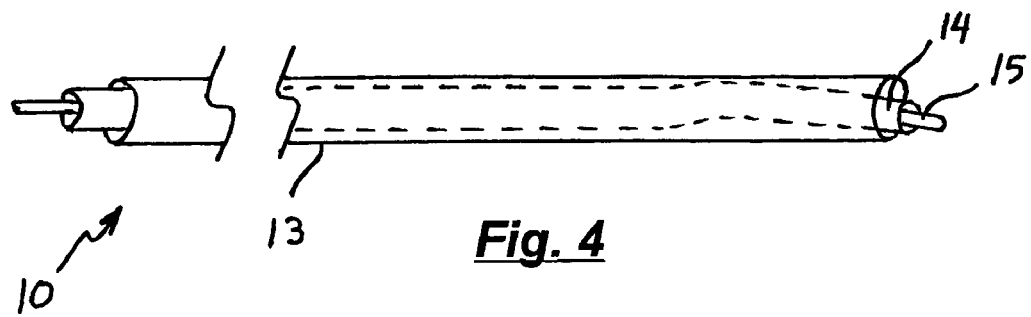
FIG. 4 is a side view showing the steering sleeve and guidewire positioned within a straightening sleeve.

As shown in FIG. 4, the straightening sleeve 13 has a normally straight configuration and functions to straighten the arcuate distal end 17 of the steering sleeve 14 when it is positioned within the straightening sleeve 13. The straightening sleeve 13 is such that the steering sleeve 14 is slidably moveable along the long axis and within a lumen of the straightening sleeve 13. The straightening sleeve 13 can be comprised of stainless steel, nitinol, plastic, polymer, or any other material known to one or skill in the art to be rendered flexible.

Figure 5:
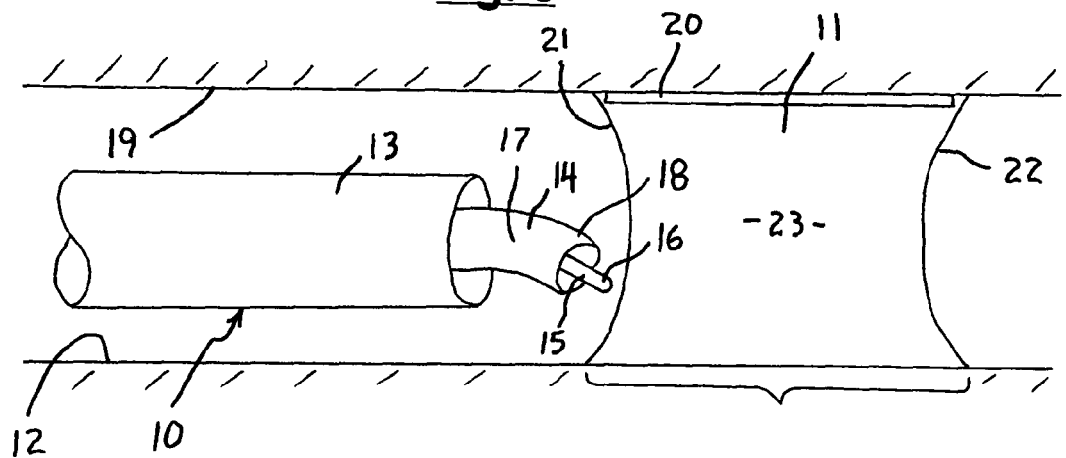
FIG. 5 shows a device of the present invention with the steering sleeve and guidewire positioned proximal to a CTO body which is to be traversed.
Figure 6:
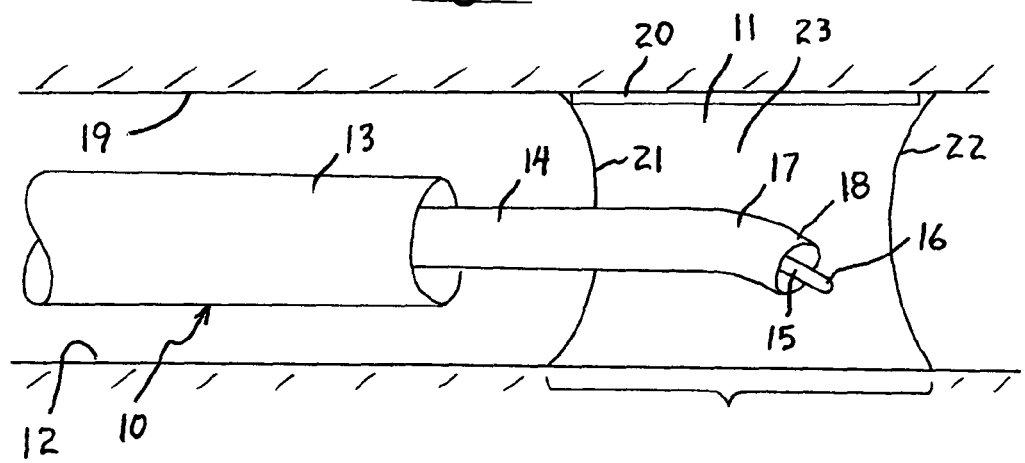
FIG. 6 shows a device of the present invention after the steering sleeve and guidewire have penetrated the proximal fibrous cap of the CTO body and are being repositioned within the CTO body to facilitate penetration of the distal fibrous cap.
Figure 7:
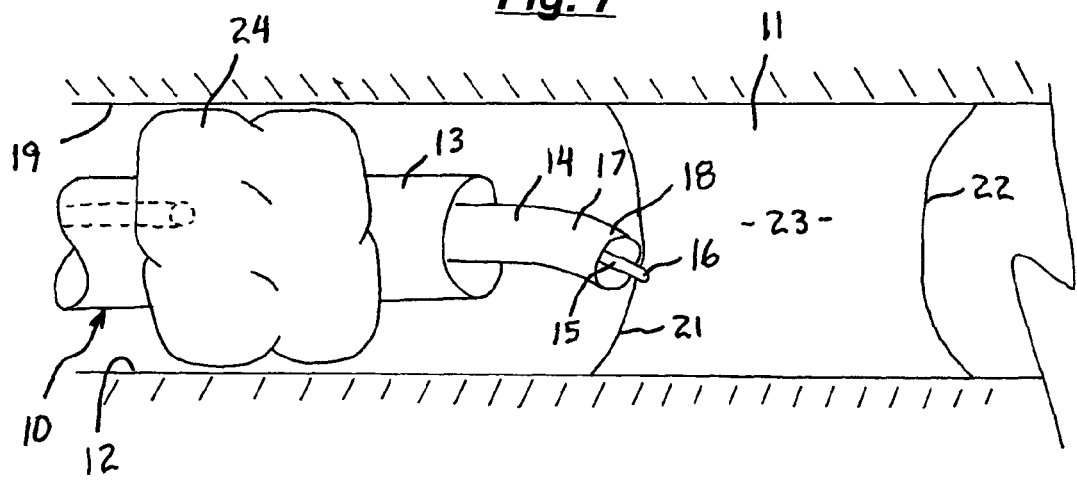
FIG. 7 shows a device of the present invention with an inflatable balloon positioned around the straightening sleeve to anchor the device in a desired position with the vessel.

The steering sleeve 14 has a first position, as shown in FIG. 4, in which the distal end 17 is straightened within the straightening sleeve 13. The steering sleeve 14 is elastic enough that it is not permanently deformed when it is straightened within the straightening sleeve 13. The steering sleeve 14 has a second position, as depicted in FIGS. 5 to 7, in which the distal end 17 extends distally past the straightening sleeve 13 to expose the preset curvature of the steering sleeve 14 to facilitate steering of the device 10 during a surgical procedure. The amount of curvature of the steering sleeve 14 during the surgical procedure is dependent upon the amount the steering sleeve 14 is exposed from the straightening sleeve 13 and whether the guidewire 15 is positioned within the steering sleeve 14. In the second position, the tip 18 of the arcuate distal end 17 of the steering sleeve 14 or the distal tip 16 of the guidewire 15 can be used for piercing, traversing and treating a CTO.

FIG. 5 shows the catheter device 10 of the present invention just prior to the penetration of a CTO body 11 by the guidewire 15. The CTO body 11 is within a blood vessel 12 having an inner wall 19. On the inner wall 19 is a plaque 20 which caused the formation of the CTO body 11 completely blocking the lumen of the vessel 12. The CTO body 11 includes a proximal fibrous cap 21, a distal fibrous cap 22, and an inner core region 23. The fibrous caps 21, 22 are typically tough and comprised mainly of hardened fibrous material. The inner core region 23 typically begins as soft plaque and is replaced by fibrous material. FIG. 5 shows the catheter device 10 deployed to a position near the proximal fibrous cap 21 of the CTO body 11 with the distal end 17 of the steering sleeve 14 extending from the straightening sleeve 13.

As shown in FIG. 7, a balloon 24 can be provided with the catheter device 10, which when inflated fits snugly within the inner wall 19 of the vessel 12. The balloon 24 functions to position and hold the straightening sleeve 13 near the CTO body 11. The straightening sleeve 13 extends beyond the balloon 24.

The steering sleeve 14 can then be used to align the appropriate "attack" angle for using the guidewire 15 to penetrate the proximal fibrous cap 21. The guidewire 15 can be advanced from the steering sleeve 14 through the proximal cap 21 and into the inner core region 23. Alternatively, the steering sleeve 14 itself can be used to penetrate the proximal cap 21 to allow the guidewire 15 to advance through the inner core region 23.

The guidewire 15 and steering sleeve 14 can move independently of one another. For example, in FIG. 6 the steering sleeve 14 is repositioned within the CTO body 11, and specifically within the inner core region 23, to facilitate aligning the guidewire 15 and ultimately the guidewire's penetration of the distal fibrous cap 22. The steering sleeve 14 can be moved to its position within the inner core region 23 via sliding movement over the guidewire 15 after the guidewire 15 traverses the inner core region 23 and abuts the distal fibrous cap 22.

Figure 8:
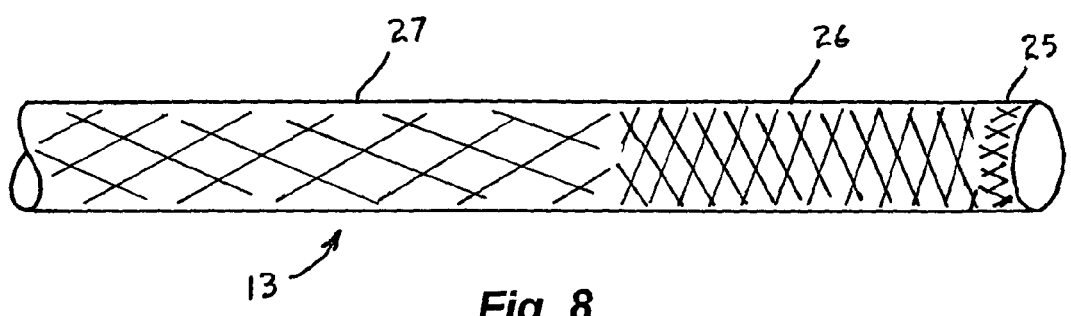
FIG. 8 is a side view of the straightening sleeve of the present invention showing regions of varied stiffness along the length of the straightening sleeve.

As shown in FIG. 8, the straightening sleeve 13 can have three regions of varied stiffness, including a rigid region 25 at the distal end, a flexible region 26 proximal to the distal end, and a semi-flexible region 27 proximal to the flexible region 26. The regions 25-27 of varied stiffness can range in length depending upon the application. For example, the rigid region 25 can be between 0.5 and 50 mm in length, and preferably between 1.0 and 10 mm. The flexible region 26 can be between 10 and 1000 mm in length, and preferably between 20 and 800 mm. The semi-flexible region 27 can be of any length desired by the treating physician.

Figure 9:
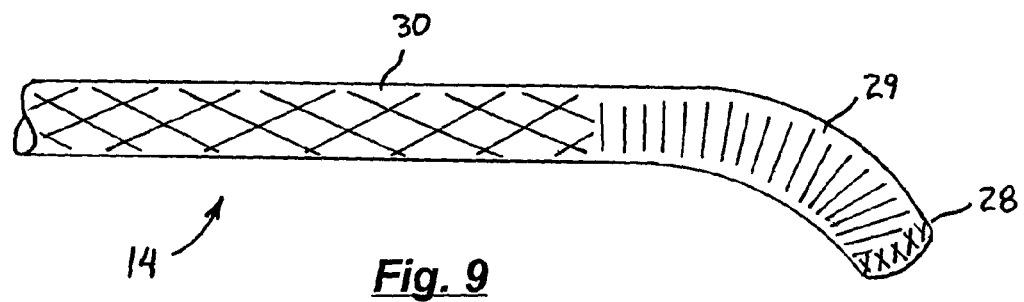
FIG. 9 is a side view of the precurved steering sleeve of the present invention showing regions of varied stiffness along the length of the steering sleeve.

As shown in FIG. 9, the steering sleeve 14 can also have three regions of varied stiffness, including a rigid region 28 at the distal end, a flexible region 29 proximal to the distal end, and a semi-flexible region 30 proximal to the flexible region 29. The regions of varied stiffness of the steering sleeve 14 can range in length depending upon the application. For example, the rigid region 28 of the steering sleeve 14 can be between 0.5 and 50 mm in length, and preferably between about 1.0 and 15 mm. The flexible region 29 of the steering sleeve 14 can be between 10 and 1000 mm in length, and preferably between about 20 and 800 mm. The semi-flexible region 30 can be of any length desired by the treating physician.

A novel method for using the catheter device 10 according to the present invention will now be described. As explained above, the steering sleeve 14 will contain an over bent curve at its distal end 17. The steering sleeve 14 is inserted into the straightening sleeve 13 until it is just ready to exit the straightening sleeve 13, and the guidewire 15 is not yet inserted into the steering sleeve 14. The catheter device 10 is then advanced into the patient's body to the treatment point. Since the guidewire 15 is not inserted at this point, the catheter device 10 will be relatively floppy and will pass tortuous anatomy fairly easy. Once in the proper position, the guidewire 15 is then inserted all the way to the distal tip 18 of the steering sleeve 14. The guidewire 15 and steering sleeve 14 are then pushed out of the straightening sleeve 13 and the combination of the over curve and the straightening force of the guidewire 15 will result in a properly shaped curve. The guidewire 15 can then be advanced out of the steering sleeve 14 to perforate the proximal cap 21 of the CTO 11. The guidewire 15 will extend generally in a straight line out of the steering sleeve 14 because only the steering sleeve 14 is curved.

Improved hub assemblies for use with the catheter device described above will now be explained with reference to FIGS. 10 to 17. The hub assemblies can be used to give the treating physician the ability to manipulate and lock the straightening sleeve 13, steering sleeve 14, and guidewire 15 together in any combination so that the components remain in the same relative position to one another and/or advanced together.

FIG. 10 shows a first hub assembly 35 attached to an outer sleeve 36 (e.g., the straightening sleeve) of the catheter, and a second hub assembly 37 attached to an inner sleeve 38 (e.g., the steering sleeve). A first locking mechanism 39 is associated with the first hub assembly 35. The first locking mechanism 39 is movable between a locked condition in which the outer and inner sleeves 36, 38 are locked together, and an unlocked condition in which the outer and inner sleeves 36, 38 are moveable relative to each other. The first locking mechanism 39 can be a mechanical lock, such as a conventional compression or friction lock.

A first motion limiting structure 40 is attached to the first hub assembly 35 for limiting a range of relative linear movement between the outer sleeve 36 and the inner sleeve 38 when the first locking mechanism 39 is in its unlocked condition. The first motion limiting structure 40 includes a first tubular segment 41 having a threaded female coupler 42 at one end and a raised flange 43 at the other end. The threaded female coupler 42 is connected to a corresponding threaded male coupler 44 on the proximal side of the first hub assembly 35. The end of the first tubular segment 41 with the raised flange 43 is slidably contained within a corresponding structure 45 on the distal side of the second hub assembly 37. When the threaded coupler 42 of the first tubular segment 41 is fastened to the first hub assembly 35, the first and second hub assemblies 35, 37 are effectively connected together by the first motion limiting structure 40. In this condition, the second hub assembly 37 is allowed to rotate and move linearly relative to the first tubular segment 41, and hence relative to the first hub assembly 35, within the limited range allowed by the opposing surfaces 46, 47 of the second hub assembly 37 that engage the raised flange 43 of the first tubular segment 41. The outer and inner sleeves 36, 38 can still be locked together against any relative movement using the first locking mechanism 39. A detent mechanism 48 can be included in the first motion limiting structure 40 for providing controlled incremental movement between the outer and inner sleeves 36, 38.

A second locking mechanism 49 is associated with the second hub assembly 37. The second locking mechanism 49 is movable between a locked condition in which the inner sleeve 38 is locked together with the guidewire 15, and an unlocked condition in which the inner sleeve 38 and the guidewire 15 are movable relative to each other. The second locking mechanism 49 can have a construction similar to the first locking mechanism 39, such as a conventional compression or friction lock.

A second motion limiting structure 50 is attached to the second hub assembly 37 for limiting a range of relative linear movement between the inner sleeve 38 and the guidewire 15 when the second locking mechanism 49 is in its unlocked condition. The second motion limiting structure 50 is similar in construction to the first motion limiting structure 40 described above. The second motion limiting structure 50 includes a second tubular segment 51 having a threaded female coupler 52 at one end and a raised flange 53 at the other end. The threaded female coupler 52 is connected to a corresponding threaded male coupler 54 on the proximal side of the second hub assembly 37. The end of the second tubular segment 51 with the raised flange 53 is slidably contained within a corresponding structure 55 on the distal side of a third hub 56 or other suitable structure connected to the guidewire 15. When the threaded coupler 52 of the second tubular segment 51 is fastened to the second hub assembly 37, the second hub assembly 37 and the third hub 56 are effectively connected together by the second motion limiting structure 50. In this condition, the third hub 56 is allowed to rotate and move linearly relative to the second tubular segment 51, and hence relative to the second hub assembly 37, within the limited range allowed by the opposing surfaces of the third hub 56 that engage the raised flange 53 of the second tubular segment 51. The second locking mechanism 49 can still be used to lock the inner sleeve 38 together with the guidewire 15. A detent mechanism 57 can be included in the second motion limiting structure 50 for providing controlled incremental movement between the inner sleeve 36 and the guidewire 15.

FIG. 11 shows another embodiment of hub assemblies which does not include motion limiting structures. In this embodiment, the first hub assembly 60 includes a first locking mechanism 61 for locking together the inner and outer sleeves 62, 63, and the second hub assembly 64 includes a second locking mechanism 65 for locking together the inner sleeve 62 and the guidewire 66.

FIG. 12 shows another embodiment of hub assemblies in which a first guide tube 70 extends from a proximal end of the first hub assembly 71, and a second guide tube 72 extends from a proximal end of an inner sleeve or guidewire 73. The second guide tube 72 is slidably received in the first guide tube 70 to aid in the handling of the device during use. The guide tubes 70, 72 can be either molded into the respective hub assemblies 71, 74, as depicted by the second guide tube 72 in FIG. 12, or attached as a separate sleeve using a threaded coupling 75 or other suitable connection, as depicted by the first guide tube 70. FIG. 13 shows a guide tube 76 having a split sidewall 77 to facilitate attachment as a separate component over the inner sleeve or the guidewire 73, and FIG. 14 shows a guide tube 78 having a central bore 79 which can be molded as an integral unit with the hub assemblies 71, 74.

Figure 16:
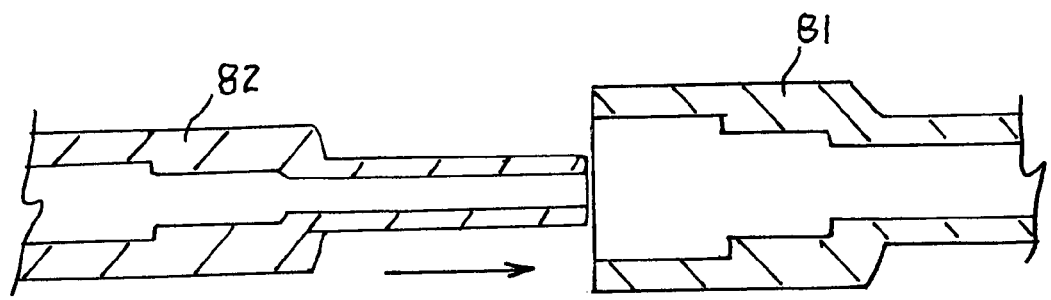
FIG. 16 is a cross section view of a hub configuration with nesting components.
Figure 17:
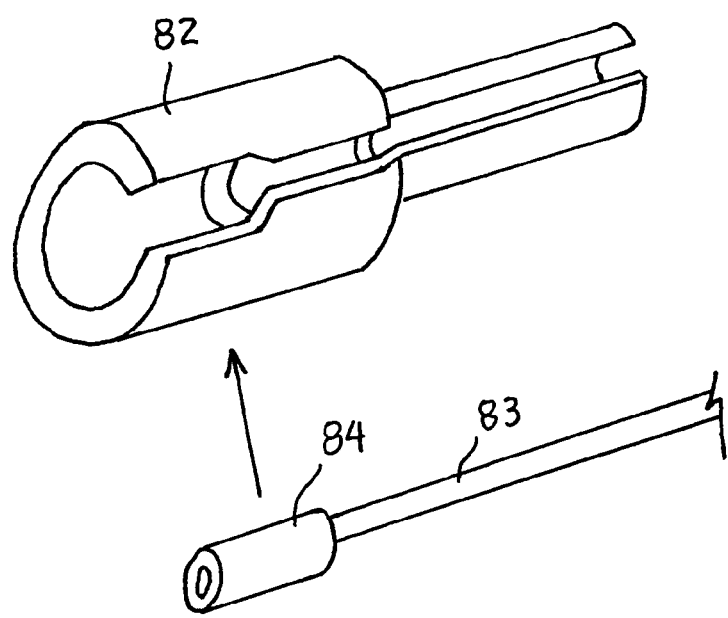
FIG. 17 is a perspective view of a the hub configuration shown in FIG. 16.

FIG. 15 shows an assembly of guide tubes 80, 81, 82 that can be snapped over the sleeves and the guidewire 83 and used with the hub configurations of the present invention. FIGS. 16 and 17 show additional details of these guide tubes 80-82.

As shown in FIG. 15, a first guide tube 80 is connected to the first hub assembly and/or the outer sleeve, a second guide tube 81 is connected to the second hub assembly and/or the inner sleeve, and a third guide tube 82 is connected to the guidewire 83. The guidewire 83 has a head 84 secured to its proximal end, which is received in a corresponding structure 85 within the third guide tube 82. The third guide tube 82 is slidably received within the second guide tube 81, and the second guide tube 81 is slidably received within the first guide tube 80. The guide tubes 80-82 can be made using materials that will allow smooth and controllable sliding movement between the parts to aid the surgeon in slidably positioning the inner and outer sleeves and the guidewire relative to each other.

While the invention has been described in connection with specific embodiments thereof, it is to be understood that this is by way of illustration and not of limitation, and the scope of the appended claims should be construed as broadly as the prior art will permit.

What is claimed is:

1. A medical device for traversing an occlusion in a vessel, comprising:
   a straightening sleeve positioned at a distal aspect of a catheter;
   a steering sleeve having an arcuate distal end, said steering sleeve and said straightening sleeve being slidably moveable relative to each other such that in a first position the arcuate distal end of the steering sleeve is straightened within the straightening sleeve and in a second position the steering sleeve extends distally past the straightening sleeve to expose the arcuate distal end;
   a guidewire disposed through the steering sleeve within the straightening sleeve;
   a first hub assembly attached to said straightening sleeve, said first hub assembly having a first locking mechanism with a locked condition in which the straightening sleeve and the steering sleeve are secured together, and an unlocked condition in which the straightening sleeve and the steering sleeve are moveable in a linear direction relative to each other;

a first motion limiting structure attached to said first locking mechanism for limiting a range of relative linear movement between said straightening sleeve and said steering sleeve when the first locking mechanism is in its unlocked condition, said first motion limiting structure comprising a first set of opposing surfaces that define respective ends of a path of linear movement between said straightening sleeve and said steering sleeve, said first motion limiting structure allowing relative linear movement between said straightening sleeve and said steering sleeve within a limited range defined by said first set of opposing surfaces;

a second hub assembly attached to said steering sleeve, said second hub assembly having a second locking mechanism with a locked condition in which the steering sleeve and the guidewire are secured together, and an unlocked condition in which the steering sleeve and the guidewire are moveable in a linear direction relative to each other; and a second motion limiting structure attached to said second locking mechanism for limiting a range of relative linear movement between said steering sleeve and said guidewire when the second locking mechanism is in its unlocked condition, said second motion limiting structure comprising a second set of opposing surfaces that define respective ends of a path of linear movement between said steering sleeve and said guidewire, said second motion limiting structure allowing relative linear movement between said steering sleeve and said guidewire within a limited range defined by said second set of opposing surfaces.

2. The medical device according to claim 1, further comprising a balloon associated with the catheter for positioning and holding the straightening sleeve near an occlusion.

3. The medical device according to claim 1, wherein said arcuate distal end of the steering sleeve comprises a hard plastic material and has a smaller outer diameter than a proximal region of the steering sleeve adjacent to the distal end.

4. The medical device according to claim 1, wherein said arcuate distal end of the steering sleeve is tipped to form a needle tip to facilitate piercing an occlusion.

5. The medical device according to claim 1, wherein said arcuate distal end of the steering sleeve is tipped to form a pointed tip to facilitate piercing an occlusion.

6. The medical device according to claim 1, wherein said arcuate distal end of the steering sleeve contains a preset curvature, and said guidewire has a preset straight configuration that imparts a straightening force on said arcuate distal end which reduces said preset curvature, said guidewire being sufficiently stiff to be used for perforating an occlusion.

7. The medical device according to claim 1, wherein said straightening sleeve has regions of varying flexibility along its length.

8. The medical device according to claim 7, wherein said regions of varying flexibility include a rigid region at the distal end, a semiflexible region at the proximal end, and a flexible region between said rigid and semiflexible regions.

9. The medical device according to claim 1, wherein said steering sleeve comprises a J-tipped needle with an arcuate shape at its distal end, and said steering sleeve being elastic enough at its distal end to be straightened without permanent deformation.

10. The medical device according to claim 9, wherein said steering sleeve has regions of varying flexibility along its length.

11. The medical device according to claim 10, wherein said steering sleeve regions of varying flexibility include a rigid portion at the distal end, a semiflexible region at the proximal end, and a flexible region between said rigid and semiflexible steering sleeve regions.

12. The medical device according to claim 1, wherein said first and second hub assemblies are connected together by said first motion limiting structure.

13. The medical device according to claim 1, wherein said first motion limiting structure comprises a detent mechanism located at increments along said linear path of movement between said first set of opposing surfaces for providing controlled incremental movement between said straightening sleeve and said steering sleeve.

14. The medical device according to claim 1, wherein said second motion limiting structure comprises a detent mechanism located at increments along said linear path of movement between said second set of opposing surfaces for providing controlled incremental movement between said steering sleeve and said guidewire.

15. The medical device according to claim 1, wherein said first motion limiting structure comprises a first tubular segment having a raised flange at one end which is slidably contained within a structure having said first set of opposing surfaces that define respective ends of a path of movement for said first tubular segment, said first set of opposing surfaces being arranged to engage the raised flange of said first tubular segment for limiting the range of linear movement of said first tubular segment in an axial direction.

16. The medical device according to claim 15, wherein said second motion limiting structure comprises a second tubular segment having a raised flange at one end which is slidably contained within a structure having said second set of opposing surfaces that define respective ends of a path of movement for said second tubular segment, said second set of opposing surfaces being arranged to engage the raised flange of said second tubular segment for limiting the range of linear movement of said second tubular segment in an axial direction.

17. A medical device, comprising:
a first hub assembly attached to an outer sleeve of a catheter;
a second hub assembly attached to an inner sleeve of the catheter;
a first locking mechanism associated with said first hub assembly, said first locking mechanism being movable between a locked condition in which the outer and inner sleeves are locked together, and an unlocked condition in which the outer and inner sleeves are moveable relative to each other;
a second locking mechanism associated with said second hub assembly, said second locking mechanism being movable between a locked condition in which the inner sleeve is locked together with a guidewire, and an unlocked condition in which the inner sleeve and the guidewire are moveable relative to each other;
a first motion limiting structure attached to said first locking mechanism for limiting a range of relative linear movement between said outer sleeve and said inner sleeve when the first locking mechanism is in its unlocked condition, said first motion limiting structure comprising a first set of opposing surfaces that define respective ends of a path of linear movement between said outer sleeve and said inner sleeve, said first motion limiting structure allowing relative linear movement between said outer sleeve and said inner sleeve within a limited range defined by said first set of opposing surfaces; and a second motion limiting structure attached to said second locking mechanism for limiting a range of relative linear movement between said inner sleeve and said guidewire when the second locking mechanism is in its unlocked condition, said second motion limiting structure comprising a second set of opposing surfaces that define respective ends of a path of linear movement between said inner sleeve and said guidewire, said second motion limiting structure allowing relative linear movement between said inner sleeve and said guidewire within a limited range defined by said second set of opposing surfaces.

18. The medical device according to claim 17, wherein said first and second hub assemblies are connected together by said first motion limiting structure.

19. The medical device according to claim 17, wherein said first motion limiting structure comprises a detent mechanism located at increments along said linear path of movement between said first set of opposing surfaces for providing controlled incremental movement between said outer sleeve and said inner sleeve.

20. The medical device according to claim 17, wherein said second motion limiting structure comprises a detent mechanism located at increments along said linear path of movement between said second set of opposing surfaces for providing controlled incremental movement between said inner sleeve and said guidewire.

21. The medical device according to claim 17, further comprising a first guide tube extending from a proximal end of the first hub assembly and a second guide tube extending from a proximal end of the inner sleeve or the guidewire, said second guide tube being slidably received in said first guide tube to aid in the handling of the device during use.

22. The medical device according to claim 17, wherein said first motion limiting structure comprises a first tubular segment having said raised flange at one end which is slidably contained within a structure having a first set of opposing surfaces that define respective ends of a path of movement for said first tubular segment, said first set of opposing surfaces being arranged to engage the raised flange of said first tubular segment for limiting the range of linear movement of said first tubular segment in an axial direction.

23. The medical device according to claim 22, wherein said second motion limiting structure comprises a second tubular segment having said raised flange at one end which is slidably contained within a structure having a second set of opposing surfaces that define respective ends of a path of movement for said second tubular segment, said second set of opposing surfaces being arranged to engage the raised flange of said second tubular segment for limiting the range of linear movement of said second tubular segment in an axial direction.

\* \* \* \* \*